(12) United States Patent
Michelson (10) Patent No.: US 7,819,906 B1
(45) Date of Patent: *Oct. 26, 2010

(54) METHOD FOR ARTHROSCOPIC MENISCAL REPAIR

(76) Inventor: Gary Karlin Michelson, 438 Sherman Canal, Venice, CA (US) 90291

(*) Notice: Subject to any disclaimer, the term of this patent is extended or adjusted under 35 U.S.C. 154(b) by 0 days.

This patent is subject to a terminal disclaimer.

(21) Appl. No.: 08/354,450

(22) Filed: Dec. 12, 1994

Related U.S. Application Data (63) Continuation of application No. 08/210,653, filed on Mar. 10, 1994, now abandoned, which is a continuation of application No. 07/965,069, filed on Oct. 22, 1992, now abandoned, which is a continuation of application No. 07/604,094, filed on Oct. 29, 1990, now abandoned, which is a continuation of application No. 07/279,978, filed on Dec. 5, 1988, now abandoned.

(51) Int. Cl.
- *A61B 17/84* (2006.01)
- *A61F 2/08* (2006.01)
- *A61F 2/28* (2006.01)

(52) U.S. Cl. .................. 606/323; 606/77

(58) Field of Classification Search .......... 606/60, 606/72, 73, 75, 76, 77, 96, 104, 220, 151, 606/154, 155, 213; 411/509, 510, 913
See application file for complete search history.

(56) References Cited

U.S. PATENT DOCUMENTS

| | | | | | |
|---|---|---|---|---|---|
| 1,374,713 | A | * | 4/1921 | Bell | 411/510 X |
| 3,213,745 | A | * | 10/1965 | Dwyer | 411/913 X |
| 4,338,835 | A | * | 7/1982 | Simons | 81/436 |
| 4,422,276 | A | * | 12/1983 | Paravano | 411/510 X |
| 4,548,202 | A | * | 10/1985 | Duncan | 606/220 |
| 4,590,928 | A | * | 5/1986 | Hunt et al. | 606/72 |
| 4,728,238 | A | * | 3/1988 | Chisholm et al. | 411/510 |
| 4,902,182 | A | * | 2/1990 | Lewis | 411/510 |
| 4,924,865 | A | * | 5/1990 | Bay et al. | 606/77 |
| 4,976,715 | A | * | 12/1990 | Bays et al. | 411/510 X |
| 5,152,765 | A | * | 10/1992 | Ross et al. | 606/104 X |
| 5,261,914 | A | * | 11/1993 | Warren | 606/77 |

FOREIGN PATENT DOCUMENTS

| | | | | |
|---|---|---|---|---|
| DE | 2933141 | * | 4/1980 | 606/72 |
| WO | 85 03857 | * | 9/1985 | 606/75 |

* cited by examiner

*Primary Examiner*—Danton DeMille
(74) *Attorney, Agent, or Firm*—Martin & Ferraro, LLP (57) ABSTRACT

A surgical rivet device for the repair of torn menisci and other intra-articular bodily tissues is disclosed in which the device comprises a shaft, projecting fins and a penetration head at one end and a wide rear portion. The device is inserted by a driving mechanism through both sides of the torn meniscus, compressing the tear in the meniscus between the fins near the head and the wide rear portion, holding the tear together. After insertion, the driving mechanism is separated from the rivet, leaving the rivet device in the patient. The rivet device is entirely biodegradable and absorabable by the body.

23 Claims, 9 Drawing Sheets

METHOD FOR ARTHROSCOPIC MENISCAL REPAIR

RELATED APPLICATIONS

This application is a continuation of application Ser. No. 08/210,653, filed Mar. 10, 1994, now abandoned, which is a continuation of Ser. No. 07/965,069, filed Oct. 22, 1992, now abandoned, which is a continuation of Ser. No. 07/604,094, filed Oct. 29, 1990, now abandoned, which is a continuation of Ser. No. 07/279,978, filed Dec. 5, 1988, now abandoned.

BACKGROUND

Menisci are large comma shaped cartilaginous pads interposed between the large bone ends of the knee joint. At present, the majority of meniscal tears are treated by resection of the meniscus via a formal incision (open method), or by a removal of just the torn portion of the meniscus via an arthroscopic procedure (closed), with the latter being of ever increasing popularity.

It has become apparent that all meniscal tears need not be removed, but rather that they can be repaired and salvaged by suturing. The problem thus far, however, has been that the method of repair by suturing requires that both sides of the meniscus be accessible, thereby necessitating either two surgical incisions and approaches or the use of the arhtroscope in lieu of one of those incisions. The arthroscope is a hollow, slender viewing rod, much like a small telescope, which can be used to view the interior of a joint. The use of an arthroscope requires a very small incision and it is possible to perform some limited types of surgery entirely with the arthroscope alone. However, this has not proven to be useful for meniscal repair.

At the present time, meniscal repair is performed in the following manner. An arthroscope is introduced through a small opening from the front of the knee joint (anteriorly) and the torn meniscus is visualized. A second small opening is also made anteriorly and a feeler device is introduced to probe the tear. These tears all occur toward the back of the knee joint (posteriorly). This is most unfortunate since this is the location of the great blood vessels and nerves of the leg. In order to repair the meniscus, therefore, one must, with significant risk, make an ample incision and surgical approach so as to expose the back of the knee joint in the region of the meniscus to be repaired. But even then there is precious little working room, and since the needles used to sew the meniscus back in place must be quite long, as they can only be passed from front to back as otherwise there would be no reliable way to tie the ends within the joint, they may cause innocent and vital structures to be either penetrated or entrapped and subsequently damaged. Hollow metal guards have been used to help direct the paths of the needles used to limit the possibility of such damage.

Therefore, there is a great need for a means of achieving a meniscal repair wherein the procedure is wholly arthroscopic, can be performed anteriorly alone, and does not require the use of an additional posterior incision.

Rivet-like tabs, sometimes referred to having a penetration head, projecting flexible members and a wide rear portion have been used for attaching carpeting to a main frame of an automobile. Such devices are typically hammered directly through the carpet into a hole pre-formed in the car body. Such devices are relatively large and have no application in a surgical procedure.

SUMMARY OF THE INVENTION

The present invention comprises a small rivet-like member in the form of a shaft having flexible projection fins extending axially from the shaft, such projections preventing withdrawal of the rivet. A penetration head is located at the front of the shaft, and the rear of the shaft has a widened portion, in the form of a disc and means for removably engaging a driver member.

In use, the driver member is inserted into an opening in the rear end of the shaft and the penetration head of the rivet is then pushed through both sides of the meniscus to be healed, until the two pieces are trapped between the fins surrounding the head and the widened portion at the rear of the shaft. The flexible rearwardly angled projection fins prevent withdrawal of the shaft through the introduction hole. The driver member is then removed from the rear opening. Additional rivets are employed, depending on the size of the tear in the meniscus. The two pieces of meniscus are thus held in place by the rivet. The rivet remains in the body and is totally biodegradable and reabsorbable.

The present invention is safer than prior devices because it does not require a second incision, that incision usually being quite major, and since it can be deployed through the small portal already present to perform the diagnostic portion of the arthroscopy, it is more efficient than prior art. Accordingly, it does not threaten the neurovascular structures which would be interposed between the open incision and the inside of the knee joint. Because of the ability of escape the extra incision, there is decreased chance of infection and decreased tissue damage. Because this device can be utilized without additional surgery, it is more efficient than the prior art. Also, because it is specifically designed to bring meniscal fragments back together, and the prior art simply utilizes sutures, it is also more effective than prior systems.

OBJECTS OF THE PRESENT INVENTION

It is an object of the present invention to provide for a device for arthroscopic meniscal repair which is safer, not requiring additional operational procedures.

It is another object of the present invention to provide for a device for arthroscopic meniscal repair which is more efficient, being able to be inserted quickly, and with a minimum of trauma.

It is another object of the present invention to provide for a device for arthroscopic meniscal repair which is more effective and simpler to use.

It is another object of the present invention to provide a device which can be used generally to attach soft tissue to bone.

These and other objects of the present invention will be apparent from a review of the following specification and the accompanying drawings.

DETAILED DESCRIPTION OF THE PRESENT INVENTION

Referring to FIGS. 1-4, the preferred embodiment of the present invention is shown. The rivet 10 consists of a tubular shaft 12 having a cone shaped penetration head at one end. A series of axial projections 16 extend from the shaft, spaced apart from one another. The projections 16 are slightly sloped away from the projection head 14. The projections 16 extend only about one half the length of the shaft 12. A widened portion, in the form of a wide circular disc 18, is formed at the rear end 20 of shaft 12. The disc 18 is circular in shape and is beveled around its circumference 22.

Figure 1:
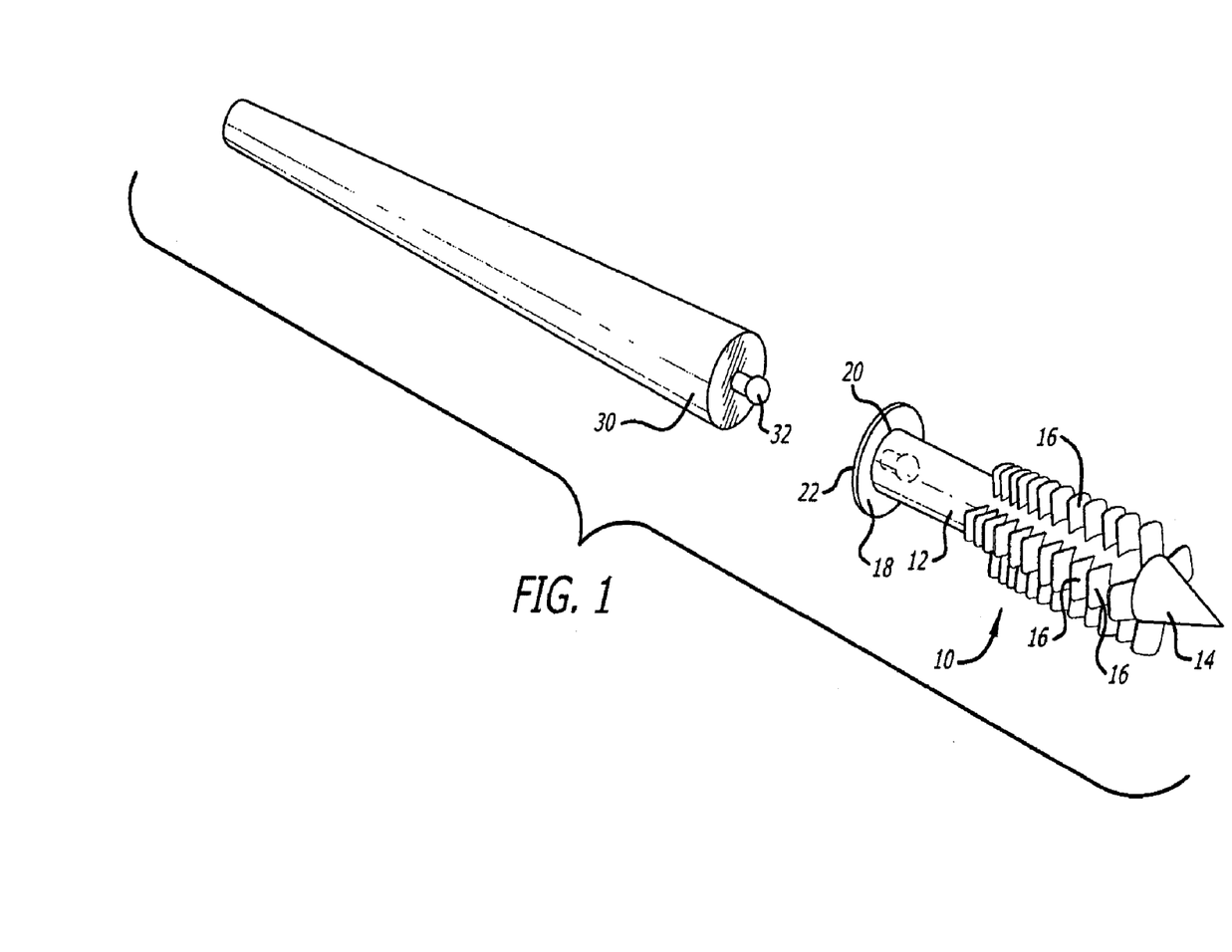
FIG. 1 is a perspective view of the rivet of the present invention and a partial view of the driver.

The rear end 20 of the shaft 12 has a depression 24 in the form of a sphere. The depression 24 is designed to engage a complementary projection 32 at the end of driver 30. The projection 32 has a slightly smaller diameter than the depression 24 in the rear 20 of the rivet 10. The projection 32 of the driver 30 fits within the depression 24 in the same manner that toy pop beads engage one another.

Figure 2:
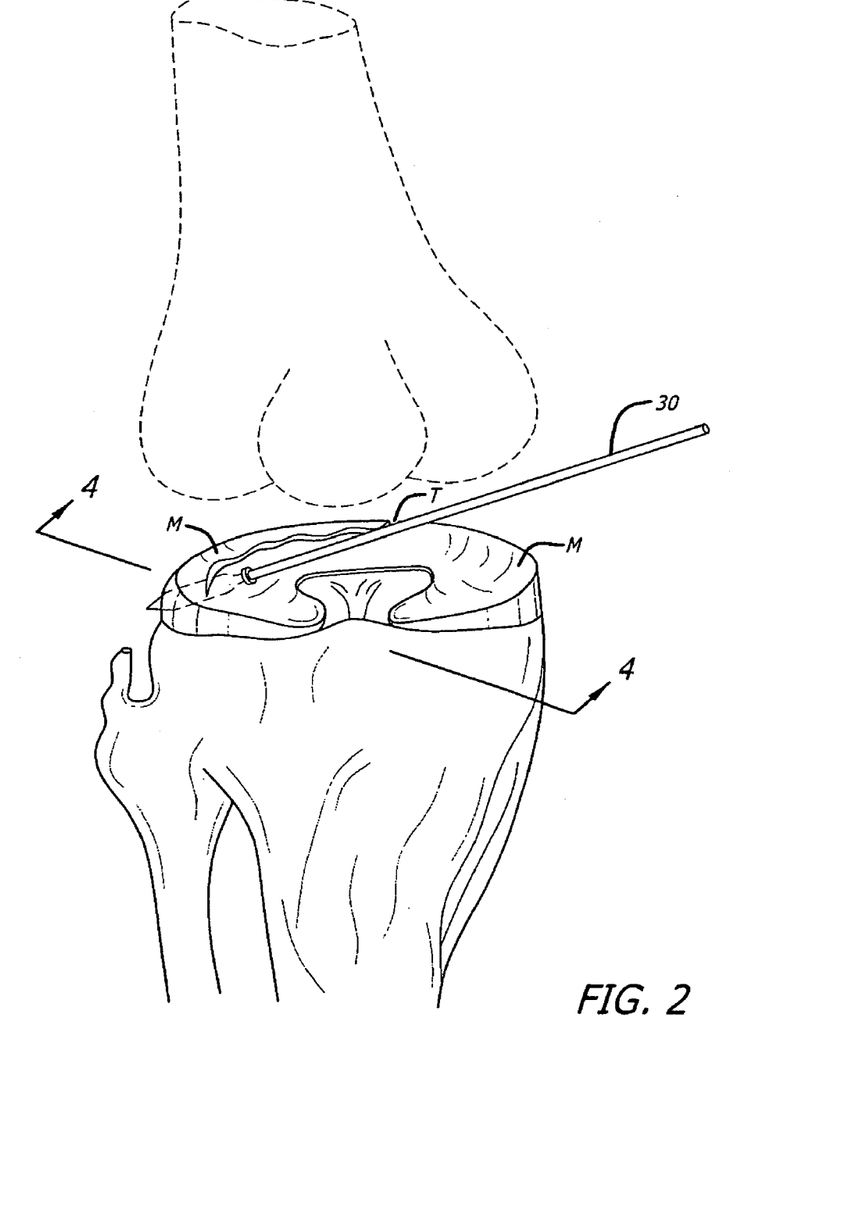
FIG. 2 is a perspective view of the human knee joint showing the rivet of the present invention being passed through the meniscus and capsule.
Figure 3:
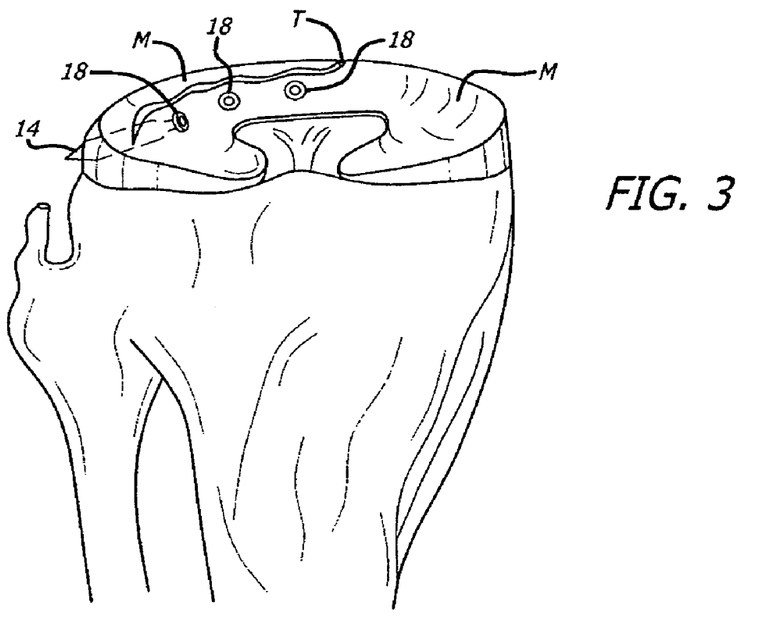
FIG. 3 is a partial sectional side view of the present invention showing the rivet of the present invention in the deployed position.
Figure 4:
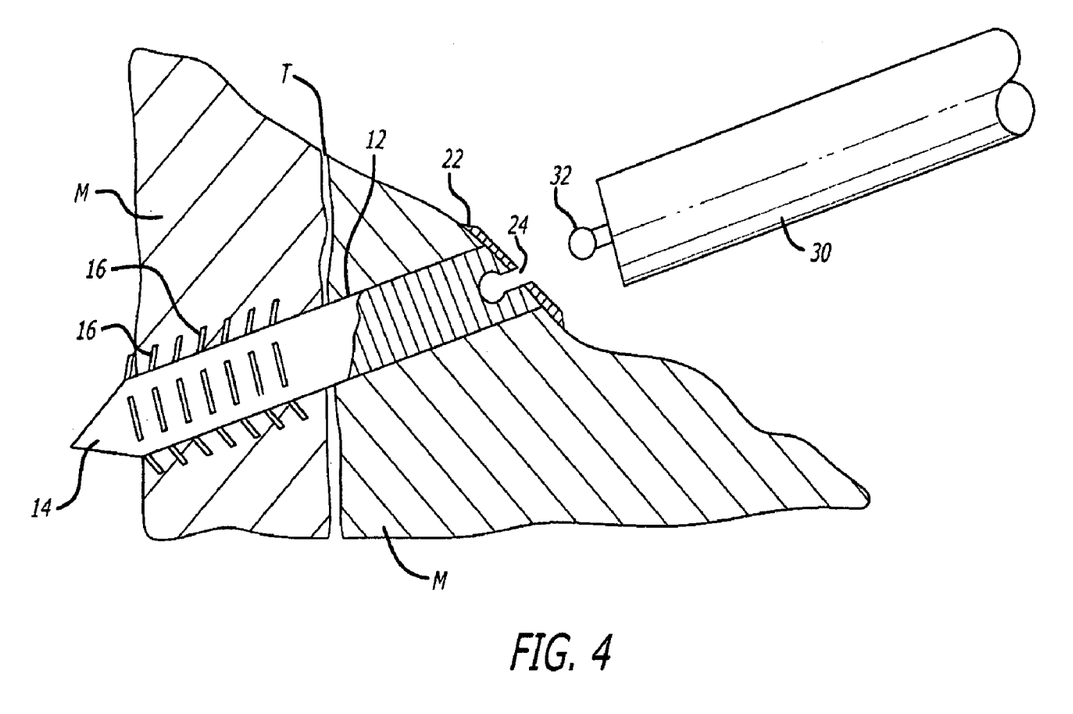
FIG. 4 is a partial sectional side view of the present invention taken along lines 4-4 of FIG. 2.

The use of the rivet 10 in operation is shown in FIGS. 2-4. The rivet 10 is attached to the driver 30 by having the rivet engaging projection 32 of the driver 30 pressed within the depression 24 in the rivet 10. The rivet 10 is then pushed through the meniscus M on one side of the tear T and through the other side of the tear T in the meniscus M. The meniscus is compressed between the fine 16 surrounding the tip 14 and the disc 18, pushing the tear T together. After insertion of the rivet 10 in the meniscus, the driver 30 is pulled rearward, disengaging the projection 32 from the depression 24 in the rear 20 of the rivet 10 due to the fact that the projections 16 prevent the withdrawal of the rivet 10. As shown in FIG. 3, additional rivets 10 may be inserted until the entire tear T is held together.

The rivet 10 is made of a soft flexible plastic which is biodegradable and totally absorbable within the body, such as polyglycolic acid or carbon composite, or any similarly biodegradable, bioabsorbable and otherwise biologically safe material. The disc 18, as shown in FIG. 4, is sufficiently flexible so as to be able to conform to the angle of the meniscus M.

Figure 5:
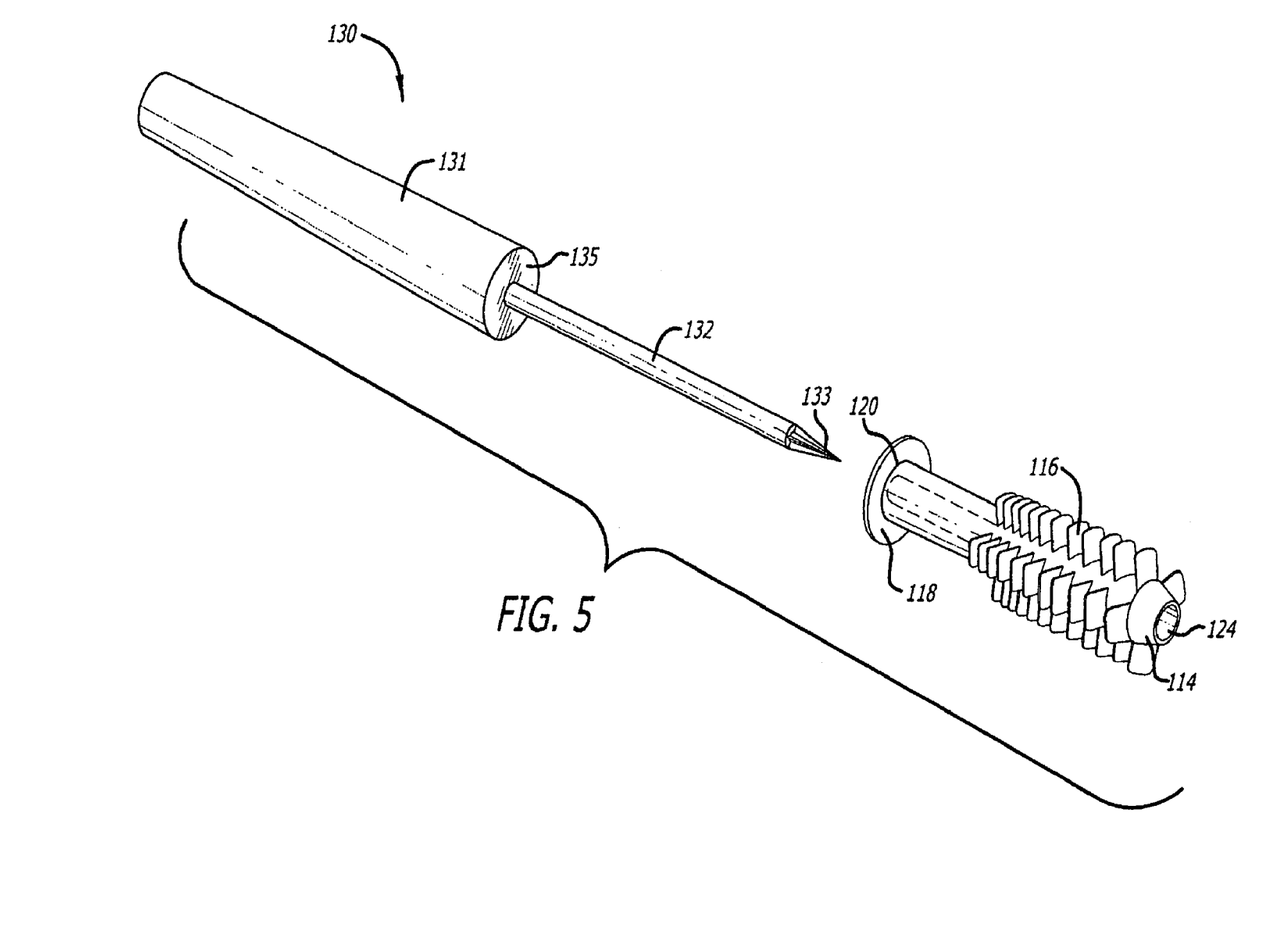
FIG. 5 is a perspective view of an alternative embodiment of the present invention.

Referring to FIG. 5, an alternative embodiment of the invention is disclosed which is easier to drive through the meniscus. The rivet 100 comprises a shaft 112 having a head portion 114 in the shape of a truncated cone. A series of projections 116 extend substantially radially from the from the upper half of the shaft 112 and slightly to the rear to prevent withdrawal of the rivet after insertion. The rear 120 of the rivet 100 has a widened disc 118. The rivet 100 is hollow along its central axis creating a passageway 124 through the entire length of the rivet 100.

The driver 130 associated with rivet 100 comprises a handle 131 having a shaft 132 terminating in a sharp tip 133. The forward face 135 of the handle 131 at the juncture of the shaft 132 and the handle 131 is flat so as to conform to the flat shape of the disc 118, and has a diameter slightly larger than the diameter of the disc 118. The diameter of the shaft 132 is slightly smaller than the inside diameter of the passageway 124.

The tip 133 of the shaft 132 is tapered so as to have substantially the same angle as the angle of the cone of the head 114, thereby forming a smooth transition from the head 114 to the tip 133.

Figure 6:
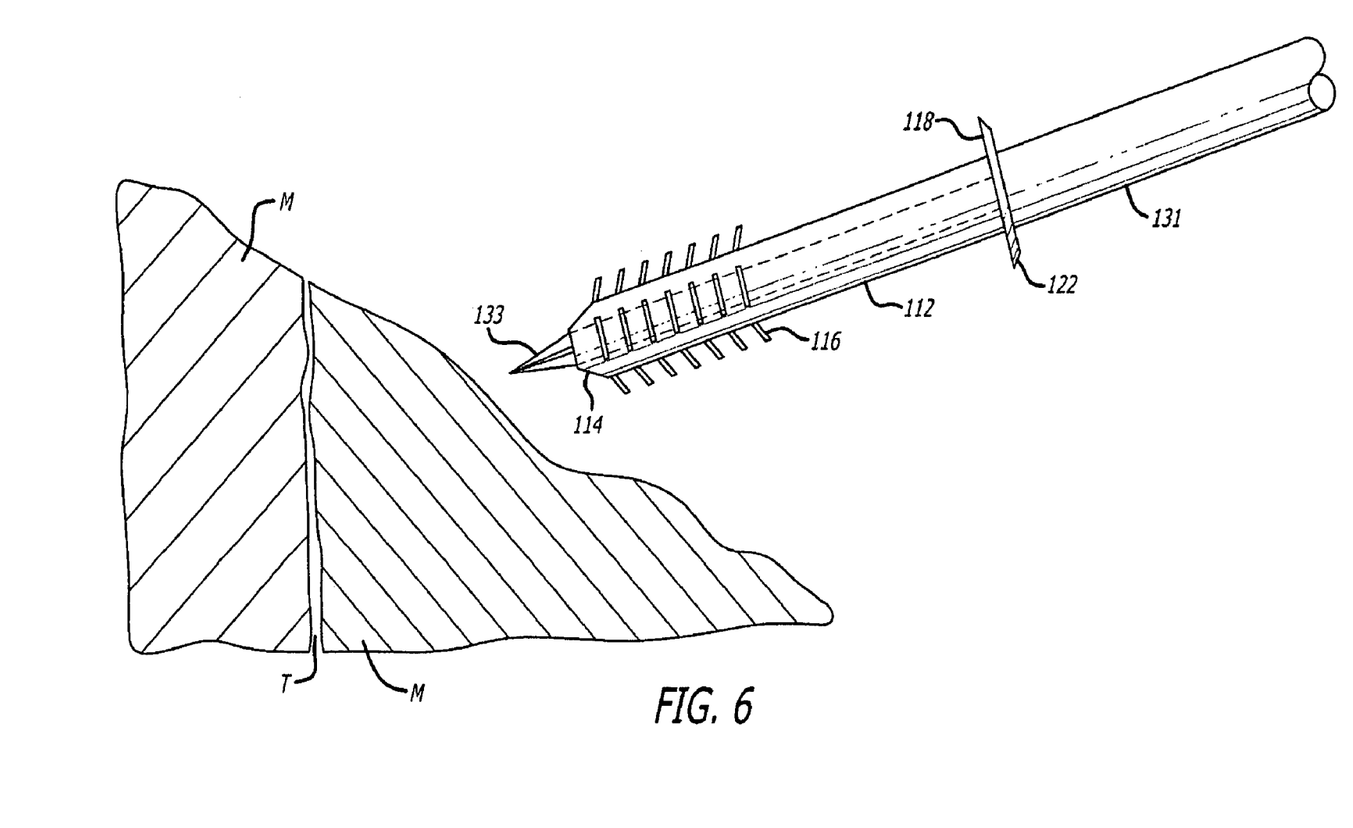
FIG. 6 is an expanded view of the driver of the alternative embodiment within the rivet.
Figure 7:
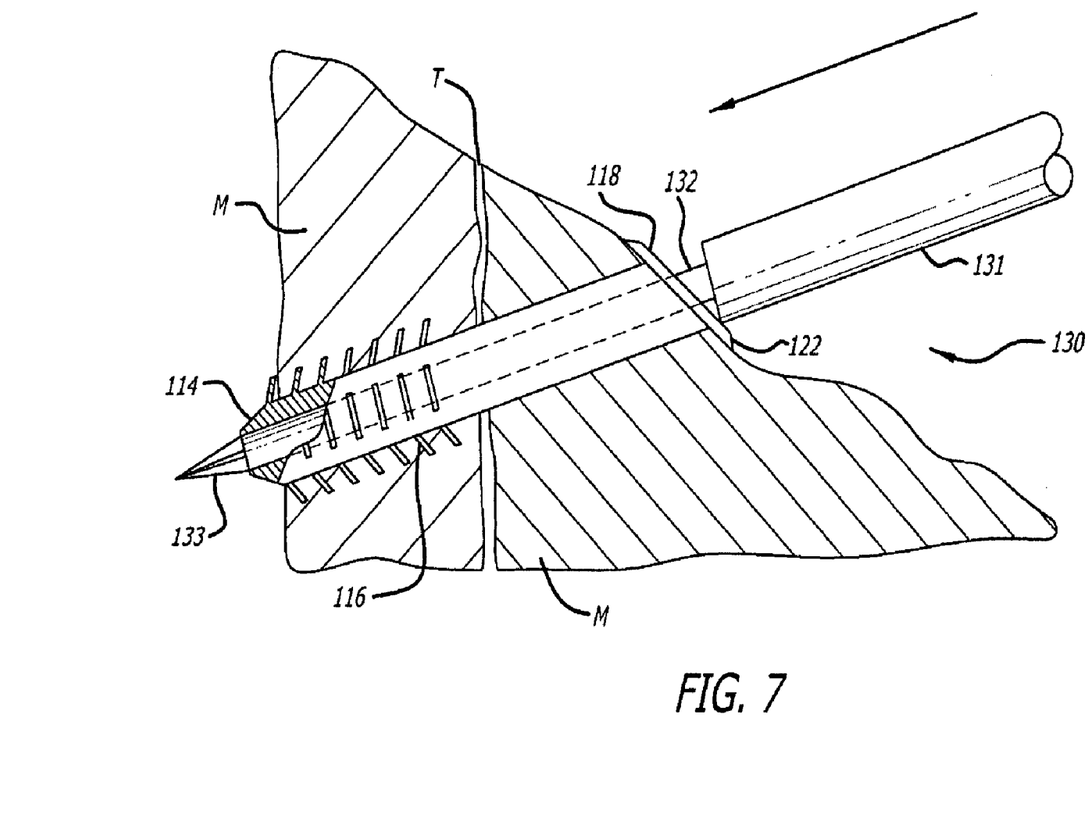
FIG. 7 is an expanded view of the driver and rivet of the alternative embodiment within the meniscus.
Figure 8:
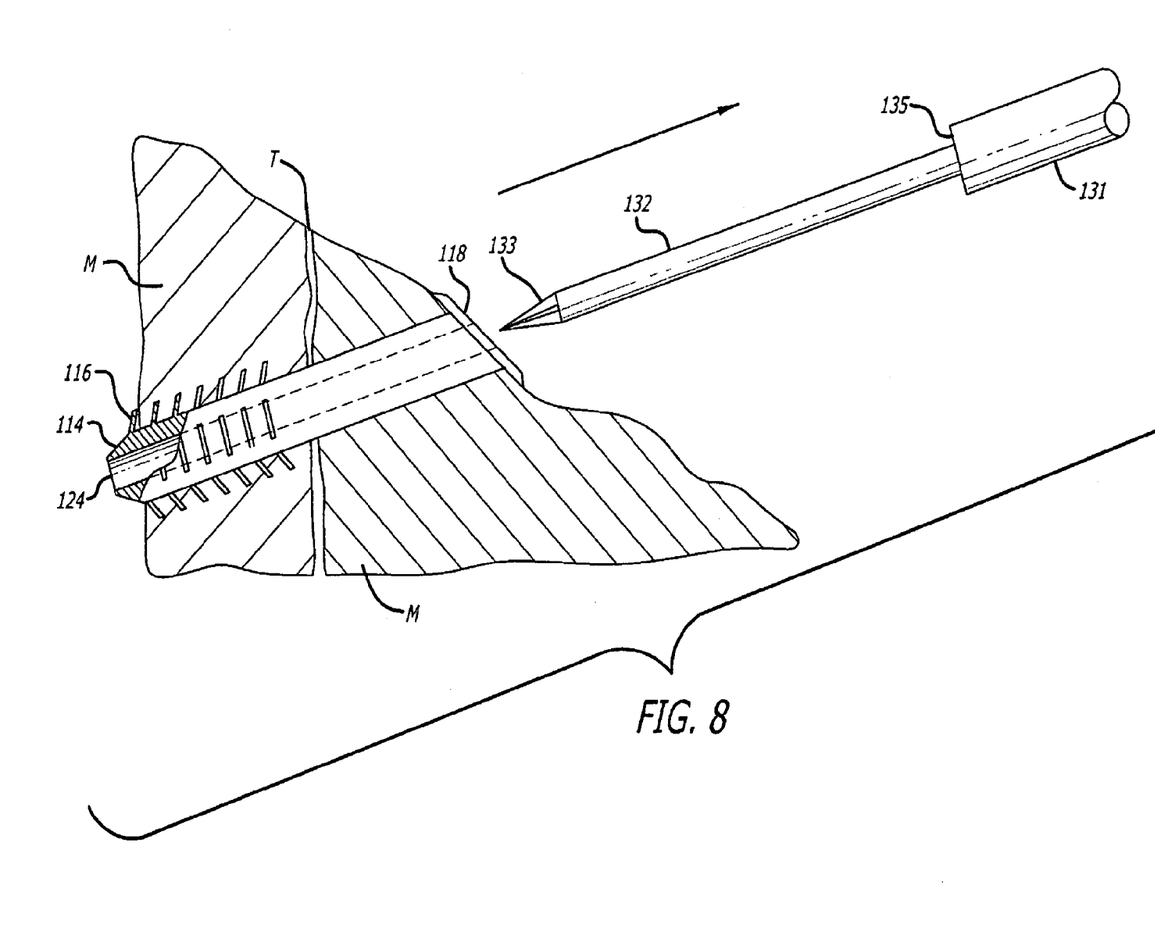
FIG. 8 is a side sectional view of the alternative embodiment of the rivet with the driver removed.

The use of the rivet is best shown by reference to FIGS. 6 and 7. The shaft 132 is passed through the passageway 124 in the rivet 100 until the rear 120 of the disc 118 abuts the flat face 135 of the handle 131. The length of the shaft 132 is such that when the rivet 100 is seated on the flat face 135, the tip 133 of the shaft 132 is in position to form a smooth transition with the head 114 of the rivet 100.

The shaft 132 of the driver 130 with the rivet 100 in place is then pushed through the meniscus M until the tear T is compressed. The force on the face 135 of the driver 130 causes the disc 118 to deform so as to conform to the surface of the meniscus, as shown in FIGS. 6 and 7. The beveled edges 122 of the disc 118 and the projecting fins 116 prevent dislodging the rivet 100 from the meniscus M. Once the rivet 100 is in the meniscus M, the driver 130 can easily be withdrawn and another rivet 100 placed on the driver and the process repeated.

The dimensions of rivet 10 are as follows: The overall length of the rivet 10 is approximately 8 mm, the shaft 12 of the rivet has an outside diameter of about 2 mm and the outside diameter of the rear disc member is about 2.5 mm.

The projection 32 of the driver 30 is slightly smaller than approximately 2 mm in diameter so as to fit within in the depression 24 in the rear of the rivet of about 2 mm. The length of the handle 30 is about 500 mm.

In the alternative embodiment of the present invention, the passageway 124 of the rivet 100 is about 1.25 mm in diameter. The shaft 132 of the driver 130 is slightly smaller than the passageway of the rivet 100 and the angle of the tip 133 and the head 114 is approximately 30-45 degrees. The tip 133 of the spear extends about 4 mm beyond the truncated end of the head 114.

Figure 9:
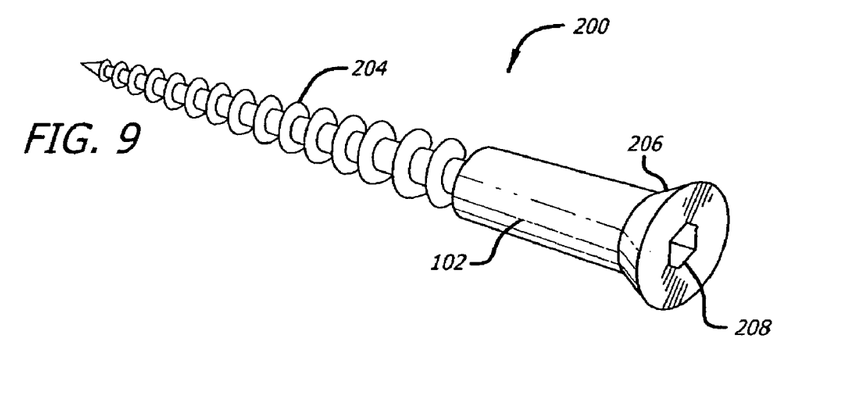
FIG. 9 is a third alternative embodiment, in the form of a screw.
Figure 10:
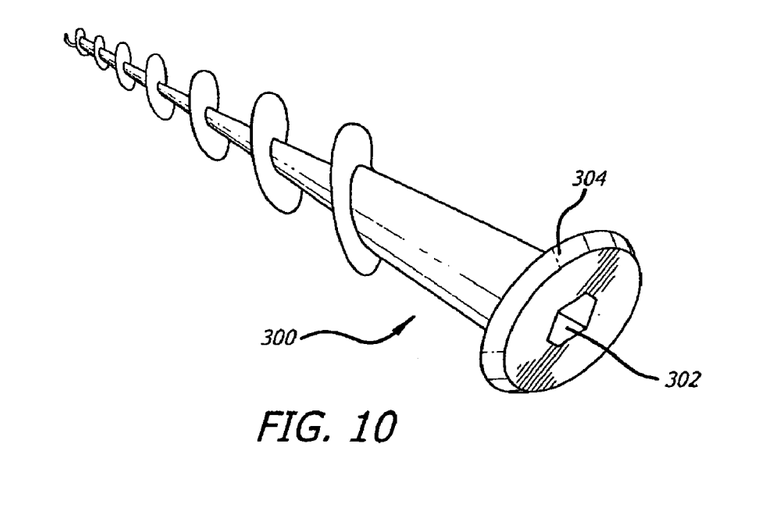
FIG. 10 is a forth alternative embodiment in the form of a screw.

Referring to FIGS. 9 and 10, alternative embodiments of the present invention are shown, in which a biodegradable screw is used in place of the rivet. Although, screws have been used before for such an application, they have been metal screws that were not biodegradable or absorbable.

In FIG. 9 the device is in the form of a screw 200, having threads 204 which extend about one half of the length of the shaft 102 screw. The tear of the meniscus would be compressed between the head 206 of the screw and the threads 204. The screw 200 is driven by an allen wrench opening 208 in the head of the screw 200.

In FIG. 10, a rivet in the form of a sheet metal screw 300 is shown. Again the screw is driven by an allen wrench opening 302 in the head 304 and the tear in the meniscus compressed between the threads of the screw 300 and the head 304 of the screw 300.

In both instances the screw of FIGS. 9 and 10 are inserted into the meniscus and then left in place. Due to the biodegradable absorbable nature of the screws, no danger is posed from the screws disengaging from the patient.

While the present inventions have been described in the concept of repairing the meniscus of the patient, it is recognized that the devices may be used in other parts of the body to repair or attach soft tissue, such as that in the shoulder where soft tissue may be desired to be attached to the bone. In such a case, a hole is drilled through the bone and then the rivet, is driven or screwed into the slightly smaller opening in the bone. The tissue is pressed against the bone and the projections or threads hold the rivet in place. The tissue reattaches itself to the bone and the rivet, being biodegradable, dissolves.

It is recognized that these and other embodiments of the invention may be devised without departing from the scope of the present invention.

What is claimed is:

1. A method for holding pieces of tissue together with a tissue rivet, the method comprising the steps of:
   providing the rivet having a shaft with a leading end for insertion first into the tissue, a trailing end opposite the leading end, a mid-longitudinal axis therebetween, and a member proximate the trailing end of the shaft, the member having a top, a bottom opposite the top, the bottom being adapted to contact tissue, at least a portion of the member being moveable relative to the shaft between an undeployed position where the bottom surface is not in contact with the tissue and a deployed position where the bottom surface contacts the tissue, the member having a first shape in the deployed position and a second shape in the undeployed position, the first shape being different from the second shape, the rivet having a passageway between the leading and trailing ends of the shaft;
   engaging a driving instrument to the rivet, the driving instrument including a handle, a shaft extending from the handle, and a face at a junction of the handle and the shaft of the driving instrument, the engaging including inserting the shaft of the driving instrument into the passageway until the face of the driving instrument contacts the top of the member;
   inserting the rivet into the tissue until the bottom contacts the tissue; and
   moving at least a portion of the member relative to the shaft to the deployed position.

2. The method of claim 1, wherein the member forms an included angle relative to the mid-longitudinal axis of the shaft of said rivet that is greater than 90 degrees.

3. The method of claim 1, wherein the member forms an included angle relative to the mid-longitudinal axis of the shaft of said rivet that is less than 90 degrees.

4. The method of claim 1, wherein the step of engaging the driving instrument with the rivet is performed so that the driving instrument does not contact the bottom of the flexible member.

5. The method of claim 1, wherein the step of inserting includes pushing the rivet into the tissue.

6. The method of claim 1, wherein the step of inserting includes inserting the rivet into a portion of a meniscus of a human knee.

7. The method of claim 6, wherein the step of inserting includes inserting the leading end of the shaft into the meniscus in a direction away from the center of the knee.

8. The method of claim 1, wherein the shaft has an exterior surface with at least one projection adapted to resist expulsion of the rivet from within the tissue, further comprising the step of compressing the pieces of tissue together between the at least one projection and the flexible member.

9. A method for holding pieces of tissue together with a tissue rivet, the method comprising the steps of:
   providing the rivet having a shaft with a leading end for insertion first into the tissue, a trailing end opposite the leading end, and a flexible member proximate the trailing end of the shaft, the flexible member having a top and a bottom opposite the top, the rivet having a passageway between the leading and trailing ends of the shaft;
   engaging a driving instrument to the rivet, the driving instrument including a handle, a shaft extending from the handle, and a face at a junction of the handle and the shaft of the driving instrument, the engaging including inserting the shaft of the driving instrument into the passageway until the face of the driving instrument contacts the top of the flexible member; and
   inserting the rivet into the tissue until the bottom of the flexible member contacts the tissue and the flexible member deforms to conform to the curvature of the tissue adjacent the rivet.

10. The method of claim 9, wherein the flexible member forms an included angle relative to the mid-longitudinal axis of the shaft of said rivet that is greater than 90 degrees.

11. The method of claim 9, wherein the flexible member forms an included angle relative to the mid-longitudinal axis of the shaft of said rivet that is less than 90 degrees.

12. The method of claim 9, wherein the step of engaging the driving instrument with the rivet is performed so that the driving instrument does not contact the bottom of the flexible member.

13. The method of claim 9, wherein the step of engaging includes snap-fitting the rivet onto a portion of the driving instrument.

14. The method of claim 9, wherein the step of inserting includes pushing the rivet into the tissue.

15. The method of claim 9, wherein the step of inserting includes inserting the rivet into a portion of a meniscus of a human knee.

16. The method of claim 15, wherein the step of inserting includes inserting the leading end of the shaft into the meniscus in a direction away from the center of the knee.

17. The method of claim 9, wherein the shaft has an exterior surface with at least one projection adapted to resist expulsion of the rivet from within the tissue, further comprising the step of compressing the pieces of tissue together between the at least one projection and the flexible member.

18. A method for holding pieces of tissue together with a tissue rivet, the method comprising the steps of:
   providing the tissue rivet having a shaft with a leading end for insertion first into the tissue, a trailing end opposite the leading end, and a member proximate the trailing end of the shaft, the member having a top, a bottom opposite the top, and an outer perimeter, the rivet having a passageway between the leading and trailing ends of the shaft;
   engaging a driving instrument to the rivet, the driving instrument including a handle, a shaft extending from the handle, and a face at a junction of the handle and the shaft of the driving instrument, the engaging including inserting the shaft of the driving instrument into the passageway until the face of the driving instrument contacts the top of the member; and
   inserting the rivet into the tissue until the bottom of the member contacts the tissue, at least a first portion of the bottom adjacent to the outer perimeter of the member being at an acute angle relative to the mid-longitudinal axis of the shaft, at least a second portion of the bottom adjacent to the outer perimeter of the member being at an obtuse angle relative to the mid-longitudinal axis of the shaft.

19. The method of claim 18, wherein the step of engaging the driving instrument with the rivet is performed so that the driving instrument does not contact the bottom of the flexible member.

20. The method of claim 18, wherein the step of inserting includes pushing the rivet into the tissue.

21. The method of claim 18, wherein the step of inserting includes inserting the rivet into a portion of a meniscus of a human knee.

22. The method of claim 21, wherein the step of inserting includes inserting the leading end of the shaft into the meniscus in a direction away from the center of the knee.

23. The method of claim 18, wherein the shaft has an exterior surface with at least one projection adapted to resist expulsion of the rivet from within the tissue, further comprising the step of compressing the pieces of tissue together between the at least one projection and the flexible member.

* * * * *